(12) United States Patent
Rasnick

(10) Patent No.: US 6,358,928 B1
(45) Date of Patent: Mar. 19, 2002

(54) PEPTIDYL SULFONYL IMIDAZOLIDES AS SELECTIVE INHIBITORS OF SERINE PROTEASES

(75) Inventor: David W. Rasnick, San Francisco, CA (US)

(73) Assignee: Enzyme Systems Products, Livermore, CA (US)

( * ) Notice: Subject to any disclaimer, the term of this patent is extended or adjusted under 35 U.S.C. 154(b) by 0 days.

(21) Appl. No.: 09/444,883

(22) Filed: Nov. 22, 1999

(51) Int. Cl.$^7$ .................. A61K 38/00; A61K 38/04; A01N 43/50; C07D 233/54; C07D 233/61
(52) U.S. Cl. .................. 514/17; 514/15; 514/16; 514/17; 514/18; 514/19; 514/20; 514/398; 514/14; 530/327; 530/328; 530/329; 530/330; 530/331; 548/335.1; 548/335.5
(58) Field of Search .................. 514/14–20, 398; 530/327–331; 548/335.1, 335.5

(56) References Cited

U.S. PATENT DOCUMENTS

| | | | |
|---|---|---|---|
| 4,518,528 A | 5/1985 | Rasnick | 260/112.5 |
| 5,656,627 A | 8/1997 | Bemis et al. | 514/221 |
| 5,716,929 A | 2/1998 | Bemis et al. | 514/18 |
| 5,776,718 A | 7/1998 | Palmer et al. | 435/23 |
| 5,804,560 A | 9/1998 | McDonald et al. | 514/19 |
| 5,807,829 A | 9/1998 | Gyorkos et al. | 514/18 |
| 5,830,870 A | 11/1998 | Iqbal et al. | 514/19 |
| 5,852,007 A | 12/1998 | Chatterjee | 514/183 |
| 5,861,377 A | 1/1999 | Fritz et al. | 514/12 |
| 5,869,725 A | 2/1999 | Gennari et al. | 556/420 |
| 5,900,400 A | 5/1999 | Thompson et al. | 514/2 |
| 5,916,888 A | 6/1999 | Peters et al. | 514/212 |

OTHER PUBLICATIONS

Toshiaki Yoshimura, Larry N. Barker and James C. Powers; Specificity and Reactivity of Human Leukocyte Elastase, Porcine Pancreatic Elastase, Human Granulocyte Cathepsin G, and Bovine Pancreatic Chymotrypsin with Arylsufonyl Fluorides; Aug. 13, 1981,; pp. 5077 through 5084.

James J. Krutak, Robert D. Burpitt, William H. Moore, and John A. Hyatt; Chemistry of Ethenesulfonyl Fluoride. Fluorosulfonylethylation of Organic Compounds; May 25, 1979; pp. 3847 through 3858.

Peter M. Tuhy and James C. Powers; Inhibition of Human Leukocyte Elastase by Peptide Chloromethyl Ketones; Dec. 2, 1974; pp. 359 through 361.

James T. Palmer, David Rasnick, Jeffrey L. Klaus, and Dieter Bromme; Vinyl Sulfones as Mechanism–Based Cysteine Protease Inhibitors; 1995; pp. 3193 through 3196.

Robert P. Hanzlik, Stewart A. Thompson; Journal of Medicinal Chemistry; Jun. 1984.

Stewart A. Thompson, Peter R. Andrews, and Robert P. Hanzlik; Carboxyl–Modified Amino Acids and Peptides as Protease Inhibitors; 1986; pp. 104 through 111.

Siming Liu and Robert P. Hanzlik; Structure—Activity Relationships for Inhibition of Papain by Peptide Michael Acceptors; 1992; pp. 1067 through 1075.

Philip J. Rosenthal, Jed E. Olson, Garson K. Lee, James T. Palmer, Jeffrey L. Klaus and David Rasnick; Antimalarial Effects of Vinyl Sulfone Cysteine Proteinase Inhibitors; Jul. 1996; pp. 1600 through 1603.

Peter M. Tuhy and James C. Powers; Inhibition of Human Leukocyte Elastase by Peptide Chloromethyl Ketones; Dec. 2, 1974; pp. 359 through 361.

James C. Powers, B. Frank Gupton, A. Dale Harley, Norikazu Nishino and Ronald J. Whitley; Specificity of Porcine Pancreatic Elastase, Human Leukocyte Elastase and Cathepsin G; Mar. 17, 1977; p. 156 through 166.

Mark O. Lively and James C. Powers; Specificity and Reactivity of Human Granulocyte Elastase and Cathepsin G, Porcine Pancreatic Elastase, Bovine Chymotrypsin and Trypsin Toward Inhibition with Sulfonyl Fluorides; 1978; pp. 171 through 179.

*Primary Examiner*—James O. Wilson
*Assistant Examiner*—Randall Winston
(74) *Attorney, Agent, or Firm*—Woodard, Emhardt, Naughton, Moriarty & McNett

(57) ABSTRACT

Novel α-amino and peptidyl sulfonyl imidazolides, a method for their synthesis, and a method for inhibiting serine proteases therewith are disclosed. Pharmaceutical compositions containing α-amino and peptidyl sulfonyl imidazolides and their use in the treatment of disease states characterized by an over-activity of serine proteases are also disclosed. Novel synthetic methods for the synthesis of sulfonyl derivatives, particularly α-amino and peptidyl sulfonyl derivatives, from thioic acid S-esters are also disclosed.

33 Claims, No Drawings

PEPTIDYL SULFONYL IMIDAZOLIDES AS SELECTIVE INHIBITORS OF SERINE PROTEASES

This invention relates generally to protease inhibitors and more particularly to peptidyl derivatives as inhibitors of serine proteases. More specifically, this invention relates to a novel class of α-amino or peptidyl compounds characterized in having a C-terminal imidazolesulfonylmethylene moiety, and being selective, irreversible serine protease inhibitors. This invention also relates to novel synthetic methods for producing sulfonyl derivatives.

BACKGROUND OF THE INVENTION

Endogenous proteases make up a large class of enzymes that are necessary in the normal turnover of proteins and peptides in living organisms. Serine proteases represent an important class of proteases characterized by an essential serine residue in the catalytic site of the enzyme. Physiologically important examples of serine proteases include trypsin, chymotrypsin, tissue kallikrein, cathepsin G, and the elastases such as leukocyte, pancreatic and human neutrophil elastases.

Protease systems are normally highly regulated to properly balance the degradative activities of cells. This regulation is in part accomplished by coordinating the synthesis of proteases with the synthesis of endogenous protease inhibitors. When the normal regulatory mechanisms become unbalanced, protease over-activity can result in devastating disease states. Elevated or unregulated protease activity has been implicated in the pathology of diseases such as respiratory distress syndrome, septic shock, multiple organ failure, emphyzema, myocardial ischemia reperfusion injury, dermatitis, cystic fibrosis, chronic bronchitis, arteriosclerosis, Alzheimer's disease, corneal ulcers, rheumatoid arthritis and acute pancreatitis, among others.

In addition to the endogenous inhibitors and their physiological roles, natural and synthetic protease inhibitors find valuable utility as research tools for biochemists and medical researchers studying protease systems, cell biology and a variety of diseases.

Despite the importance of the serine proteases and their implication in numerous disease states, effective therapies directed toward inhibition of serine proteases have been hampered by a need for greater specificity in targeted inhibition of individual serine proteases for a given disease state. Furthermore, many inhibitors to date have lacked sufficient stability under physiological conditions to be considered for therapeutic use.

It has been known that peptidyl sulfonyl fluorides, such as phenylmethylsulfonyl fluoride, can be irreversible inhibitors of serine proteases. They are selective for serine proteases in that they tend to be efficient substrates for cysteine proteases and therefore do not irreversibly inhibit cysteine proteases. However, sulfonyl fluorides are not stable under physiological conditions. They are also general inhibitors of serine proteases and are not selective for individual proteases.

Another drawback of sulfonyl fluoride derivatives has been the lack of facile procedures to produce series of tailored sulfonyl fluoride derivatives. Halosulfonyl moieties are highly reactive and it has previously been difficult to generate them or efficiently use them in synthetic pathways involving peptides due to unwanted side reactions.

Peptidyl chloromethane derivatives have also proven effective inhibitors of serine proteases, but are too reactive as general alkylating agents to be useful in vivo. These compounds tend to indiscriminately alkylate most available nucleophiles and are therefore only useful in simple, well defined research systems.

A new family of peptidyl derivatives has been discovered that overcomes these and other drawbacks to the presently known serine protease inhibitors. It has now been surprisingly found that the peptidyl sulfonyl imidazolide compounds of the present invention provide physiologically stable compounds useful as selective, irreversible inhibitors of serine proteases.

SUMMARY OF THE INVENTION

It is an object of the present invention to provide serine protease inhibitors for research and therapeutic uses. It is also an object of the invention to provide a family of inhibitors whose members may be tailored to be inhibitors of serine proteases generally, or to be selective inhibitors for specific proteases or subsets of proteases within the serine protease family. Yet another object of the present invention is to provide serine protease inhibitors that are stable under physiological conditions.

Another object of the present invention is to provide a facile synthetic route to a series of sulfonyl derivatives, particularly to α-amino or peptidyl compounds characterized by the conversion of at least one carboxy group to an imidazolesulfonylmethyl group.

Yet another object of the present invention is to provide therapeutic compositions comprising peptidyl sulfonyl imidazolides as serine protease inhibitors useful in the treatment of disease states characterized by an over-activity of one or more serine proteases. Another aspect of the present invention is to provide methods of use of such therapeutic compositions to treat such disease states.

These and other objects and aspects of the present invention are addressed by the new imidazolesulfonylmethyl peptide derivatives described herein and the novel synthetic methods used for their manufacture.

The serine protease inhibitors of the present invention are α-amino or peptidyl compounds having a C-terminal imidazolesulfonylmethyl group. In one embodiment, the inhibitor compound is characterized by the formulas

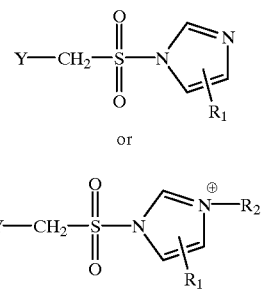

wherein Y is a group capable of interacting with the substrate recognition site of a serine protease, $R_1$ is hydrogen or branched or unbranched, substituted or unsubstituted $C_1$–$C_{12}$ alkyl, aryl, alkaryl, aralkyl or acyl, and $R_2$ is branched or unbranched $C_1$–$C_6$ alkyl. In a preferred embodiment, Y comprises an α-amino group or an amino acid chain of from 2 to 12 amino acid residues. It is preferred that the α-amino group or sequence of amino acid residues in the inhibitor compound is chosen to selectively bind to the substrate recognition site of the protease to be inhibited.

Y may also be of the formula

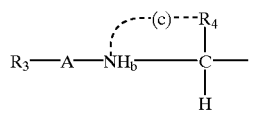

wherein $R_3$ is hydrogen or an N-terminal blocking group, A is an amino acid chain of from 0–11 amino acid residues, $R_4$ is an amino acid side chain, b=0 or 1, and c is a covalent bond when b=0 and c not a covalent bond when b=1.

When Y is an amino acid chain, each pair of amino acid residues may be linked to one another by amide bonds or by any other linkage that mimics an amide bond in a peptide. Such alternative linkages may include vinyl, ether, ketomethylene, methylketo, methylamine, aminomethyl, methylene, ethylene, cyclopropylene, thioamide and sulfonamide.

Another aspect of the present invention provides a method of inhibiting a serine protease comprising the step of contacting the protease with a peptidyl sulfonyl imidazolide compound as described above. It is preferred that the protease is contacted with at least a stoiciometric amount of the inhibitor compound and that the compound has a sequence of amino acid residues designed to selectively bind to the substrate recognition site of the protease.

Another aspect of the present invention provides a pharmaceutical composition useful in the treatment of human and animal disease states characterized by an over-activity of one or more serine proteases comprising a pharmaceutically acceptable carrier containing a therapeutically effective amount of a peptidyl protease inhibitor compound as described above. The pharmaceutical composition may be formulated for oral administration as a liquid, tablet, capsule, or enteric encapsulated solid form, or it may be formulated for parenteral or I.V. injection or for administration by infusion.

The present invention also provides for a method of treatment of mammalian disease states characterized by an over-activity of one or more serine proteases comprising administering in a pharmaceutically acceptable carrier, a therapeutically effective amount of a pharmaceutical composition as described above.

Another aspect of the present invention provides for a novel synthetic process for converting a carboxyl group on an organic molecule to a substituted or unsubstituted imidazolesulfonylmethyl group by:

i) reacting the organic molecule with an alkylchloroformate to produce an alkylformate anhydride intermediate;

ii) reducing the alkylformate anhydride intermediate with a borohydride salt to produce an hydroxymethyl intermediate;

iii) reacting the hydroxymethyl intermediate with an alkyl or arylsulfonyl chloride to produce a sulfonate intermediate;

iv) reacting the sulfonate intermediate with cesium alkyl or arylcarbothioic acid to produce a thioic acid S-ester intermediate;

v) reacting the thioic acid S-ester intermediate with $Cl_2$ and water to produce a sulfonyl chloride intermediate; and vi) reacting the sulfonyl chloride intermediate with substituted or unsubstituted imidazole to produce the imidazolesulfonylmethyl derivative.

It is particularly preferred to conduct step i) in the presence of a tertiary amine or equivalent acid scavenger to coordinate protons generated in the reaction. A preferred molar ratio of tertiary amine or acid scavenger to alkylchloroformate is at least 1.

Likewise, it is particularly preferred to conduct step vi) in the presence of a tertiary amine or equivalent acid scavenger to coordinate protons generated in the reaction. It is particularly convenient to use an excess of imidazole as the scavenger.

In a preferred embodiment of steps v) and vi) of the synthetic process, the molar ratio of water to thioic acid S-ester is at least about 2, the molar ratio of $Cl_2$ to thioic acid S-ester is at least about 3, the molar ratio of imidazole to sulfonyl chloride intermediate is at least about 1, and the molar ratio of acid scavenger to sulfonyl chloride intermediate is at least 1. A preferred method of reacting the $Cl_2$ and water with the thioic acid S-ester is to bubble chlorine gas through a liquid comprising the thioic acid S-ester and water.

In one embodiment of the synthetic method of the present invention, the organic molecule having a carboxy group is an amino acid or an amino acid chain of from 2–12 amino acid residues. One particularly useful carboxy group that may be converted to an imidazolesulfonylmethyl group with the present method is the α-carboxy group of an amino acid or the C-terminal carboxy group of an amino acid chain, though the conversion of other carboxy groups on such molecules may be as facile.

In another embodiment of the present invention, there is provided a process for converting a thioic acid S-ester compound to a sulfonyl derivative compound comprising the steps of:

i) reacting the thioic acid S-ester compound with $Cl_2$ and water to form the corresponding chlorosulfonyl intermediate; and ii) reacting the chlorosulfonyl intermediate with a nucleophile to form the corresponding sulfonyl derivative compound.

Preferred nucleophiles include imidazole, pyrazole, benzimidazole, benzotriazole, 1,2,3-triazole and 1,2,4-triazole.

It is particularly preferred to conduct step ii) in the presence of a tertiary amine or equivalent acid scavenger to coordinate protons generated in the reaction. It is convenient to use an excess of nucleophile as the scavenger.

In a preferred embodiment, the process is run with a molar ratio of water to thioic acid S-ester of at least about 2, a molar ratio of $Cl_2$ to thioic acid S-ester of at least about 3, a molar ratio of nucleophile to thioic acid S-ester of at least about 1, and the molar ratio of acid scavenger to sulfonyl chloride intermediate of at least about 1. The reaction of the thioic acid S-ester with the $Cl_2$ and water may be conducted by bubbling chlorine gas through a liquid comprising the thioic acid S-ester and water.

Further objects, embodiments, features, benefits and advantages of the present invention will be apparent to one of ordinary skill in the art from the following description of the preferred embodiments of the invention.

DESCRIPTION OF THE PREFERRED EMBODIMENTS

For the purpose of promoting an understanding of the principles of the invention, reference will now be made to preferred embodiments and specific language will be used to describe them. However, these descriptions are intended to only be exemplary to aid in a clearer understanding of the principles of the invention and not as limitations of its scope.

Alterations and modifications in the described embodiments and further applications of the principles of the invention as would normally occur to one skilled in the biochemical arts are contemplated within the scope of the present invention.

DEFINITIONS

Unless otherwise stated, the following terms used in the specification and claims shall have the following meanings for the purposes of this application:

"Peptidyl" is used in its broadest meaning, which includes, but is not limited to, chains of two or more amino acid residues linked through amide bonds. Unless otherwise stated, the amino acid residues may be from naturally occurring amino acids or from non-naturally occurring amino acids. "Peptidyl" unless otherwise stated, also includes any peptidomimetic analogue known in the art, as for example having one or more amide linkages between amino acid residues replaced with alternative linkages.

"Amino acid" is a hydrocarbon molecule having at least one amino group and at least one carboxy group as substituents. An α-amino acid is an amino acid wherein an amino group is bonded to the same carbon atom in the hydrocarbon molecule as a terminal carboxy group.

"α-carbon" or "alpha carbon" means that carbon of an α-amino acid or α-amino acid residue to which the amino group, carboxy group, hydrogen and distinctive amino acid side chain are bonded. In an amino acid residue, either the amino group or carboxy group may be modified or eliminated, in which case, the α-carbon refers to the carbon through which the amino acid side chain is linked to the rest of the molecule.

"α-Amino group" means a substituent on a molecule comprising at least an amino group bonded through the carbon atom on the substituent through which the substituent is bonded to the rest of the molecule; that is a group of the formula

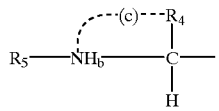

wherein $R_4$ is an amino acid side chain, $R_5$ is H or another substituent, b=0 or 1, and c is a covalent bond when b=0 and c is not a covalent bond when b=1. By "c is not a bond, it is understood that—(c)— is simply absent from the formula; there is no bond between the nitrogen and $R_4$. This does not preclude non-covalent interactions, such as ionic interactions, hydrogen bonding or Van der Waals interactions, between the nitrogen and $R_4$.

"Methylene" as in "imidazolesulfonylmethylene" means a divalent radical of the formula —$CH_2$—.

"N-terminal" and "C-terminal" are in reference to the directionality of the amino acids in an amino acid chain such that the N-terminal is that end of the chain oriented with the α-amino groups and the C-terminal is that end of the chain oriented with the α-carboxy groups.

"C-terminal carboxy group" refers to the carboxy group bonded to the α-carbon of an amino acid or the α-carbon of the C-terminal amino acid residue in an amino acid chain.

"C-terminal imidazolesulfonylmethylene group" refers to an imidazolesulfonylmethylene group bonded to an α-amino acid or the C-terminal amino acid residue in an amino acid chain in place of the C-terminal carboxyl group normally present.

Unless otherwise stated, the alpha amino acids of the compounds of the present invention are preferably in their L-configuration. α-Amino acids having the D-configuration or compounds having a racemic mixture of L- and D-α-amino acids may also be used in the present invention, however, it is commonly known that the bioactivity of molecules containing D-configuration amino acid residues may be greatly reduced due to the stereo specific nature of binding sites and active sites of most biomolecules.

"Protective group" has the meaning conventionally associated with it in synthetic organic chemistry, i.e., a group which blocks a reactive site in a compound thereby making the site unreactive until the protecting group is removed. See for example Greene et al., "Protective Groups in Organic Synthesis," second edition, John Wiley and Sons, 1991, herein incorporated by reference.

"Protected" in reference to a compound or a group means a derivative of the compound or a group in which at least one reactive site is blocked with a protective group.

"Optional" or "optionally" means that the subsequently described object, event or circumstance may or may not occur, and that the description includes instances wherein the object, event or circumstance occurs and instances in which it does not. For example, "optionally further substituted with one or more functional groups" means that the substitutents may or may not be present in order for the compound described to fall within the invention, and the invention includes those compounds wherein one or more functional groups are present and those compounds in which no functional groups are present.

As used herein unless specifically stated otherwise, when the terms "substituted" and/or "unsubstituted" are used in connection with a list of items, groups, substituents, moieties, etc., the term or terms apply to all members of the list individually as if stated separately with each member.

Unless otherwise stated, "Solution" as used herein is meant in the broader sense of a fluid and encompasses liquids, true solutions, suspensions, solid/liquid dispersions, emulsions, immiscible liquid mixtures, etc.

"Pharmaceutically acceptable" means that which is useful in preparing a pharmaceutical composition and is generally safe, non-toxic and neither biologically nor otherwise undesirable and includes that which is acceptable for veterinary use as well as human pharmaceutical use.

"Pharmaceutically acceptable salt" means a salt that is pharmaceutically acceptable as defined above and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2,2,2]oct-2-ene-1-carboxylic acid, glucoheptonic acid, $4,4^1$-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

As used herein, an "effective amount" of a compound for treating a disorder is an amount that is sufficient to ameliorate, or in some manner reduce a symptom or stop or reverse progression of a condition. Such amount may be administered as a single dose or may be administered according to a regime, whereby it is effective.

"Therapeutically effective amount" means that amount which, when administered to an animal for treating a disease includes:

1) preventing the disease from occurring in an animal which may be predisposed to the disease but does not yet experience or display symptoms of the disease, 2) inhibiting the disease, i.e., arresting its development, or 3) ameliorate the disease, i.e., causing regression of at least one symptom of the disease.

As used herein, "treatment" means any manner in which the systems or pathology of a condition, disorder, or disease are ameliorated or otherwise beneficially altered. Treatment also encompasses any pharmaceutical use of the compositions herein.

As used herein, "amelioration of the symptoms" of a particular disorder by administration of a particular pharmaceutical composition refers to any lessening, whether permanent or temporary, lasting or transient, that can be attributed to or associated with administration of the composition.

Additional abbreviations used herein are listed in Table 1.

TABLE 1

Chemical Abbreviations Used This Application

| Abbreviation* | Chemical |
| --- | --- |
| Im | Substituted or Unsubstituted Imidazole |
| THF | Tetrahydrofuran |
| DMF | Dimethylformamide |
| DMSO | Dimethyl Sulfoxide |
| EtOAc | Ethyl Acetate |
| NMM | N-methylmorpholine |
| IBCF | Isobutylchloroformate |
| EtOAc | Ethyl Acetate |
| MeOH | Methanol |
| TEA | Triethylamine |
| Mesyl-Cl | Methanesulfonyl Chloride |
| $CH_2Cl_2$ | Methylene Chloride |
| HOBT | Hydroxybenzoltriazole |
| DCC | Dicyclohexylcarbodiimide |
| HCl | Hydrochloric Acid |
| $NaHCO_3$ | Sodium Bicarbonate |
| $MgSO_4$ | Magnesium Sulfate |

*Standard three letter abbreviations used for amino acid residues in peptide chains

SERINE PROTEASE INHIBITOR COMPOUNDS

As noted above, the present invention relates to serine proteases inhibitor compounds, to compositions and therapeutic formulations containing such compounds, to the use of such compounds and compositions to inhibit serine proteases and methods to treat disease states characterized by an over-activity of serine proteases. This invention also relates to novel synthetic methods for producing sulfonyl derivatives including sulfonyl imidazolides.

The inhibitor compounds of the present invention are α-amino or peptidyl compounds having a C-terminal imidazolesulfonylmethyl group. In one embodiment, serine protease inhibitors of the present invention are characterized in having the formula

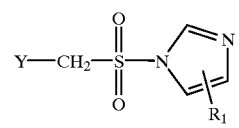

I(a)

or

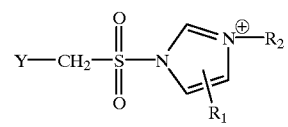

I(b)

wherein Y is a group capable of interacting with the substrate recognition site of a serine protease, $R_1$ is hydrogen or branched or unbranched, substituted or unsubstituted $C_1$–$C_{12}$ alkyl, aryl, alkaryl, aralkyl or acyl, and $R_2$ is branched or unbranched $C_1$–$C_6$ alkyl. Suitable substitutions on $R_1$ may include the incorporation of one or more functional moieties selected from the group consisting of hydroxy, amino, nitro, nitrile, guanidino, sulfinyl, sulfonyl, thiol, and halo, provided that none of the substitutions interfere with the intended function of the compound as an inhibitor.

The interaction of Y should allow the imidazolesulfonyl group to orient with the protease's active site serine residue so as to facilitate the reaction of the inhibitor compound with the serine residue, thereby inhibiting the activity by the protease.

In a preferred embodiment, Y comprises an α-amino group, or an amino acid chain of from 2 to 12 amino acid residues. The amino acid residue(s) may each be independently selected from the naturally occurring amino acids or may, alternatively, be synthetic amino acids not normally occurring in nature. The α-amino group or the number and sequence of amino acid residues in the amino acid chain are selected to tailor the specificity of the inhibitor compound to serine proteases generally or to a specific subclass (family) or individual serine protease.

Each protease molecule has one or more substrate recognition sites (or binding sites) defined by specific amino acid residues in a particular spatial arrangement that is sufficiently complimentary to a substrate molecule's structure to at least temporarily bind the substrate molecule in an orientation enabling the substrate to react with the active site of the protease. The specific activity of the protease in cleaving a given substrate correlates generally to the substrate's binding constant for the substrate recognition site. The better the match-up of hydrogen bonds, ionic interactions, and Van der Waals interactions between the substrate and the substrate recognition site, the stronger the binding and, generally speaking, the greater the protease's specific activity for that substrate. By selecting the α-amino group or amino acid sequence of a serine protease inhibitor compound of the present invention to complement the structure of the substrate recognition site of a serine protease or family of proteases of interest to a desired degree, the specific activity of an inhibitor compound can be tailored for that protease or family of proteases as desired.

While not being limited to any particular theory, it is believed that the α-amino group or amino acid residues of the present inhibitor compounds initially bind noncovalently to the substrate recognition site of the protease, whereby the imidazolesulfonylmethyl group is oriented to react with the protease's active site serine residue. It is further believed that the protease's serine residue is sulfonylated by a nucleophilic displacement reaction wherein the imidazole moiety is a leaving group and the sulfonyl moiety forms a stable sulfonate linkage with the serine residue. Substitutions on the imidazole group tend to make it a better leaving group and the compound generally more reactive. This can be used to advantage in tailoring compounds to specific proteases or systems. It is believed that the protease is inactivated by the sulfonylation of the protease's required active site serine residue.

When Y is an amino acid chain, the linkage between each pair of amino acid residues in the chain is typically an amide bond as in naturally occurring peptides and proteins. Alternatively, any one or more of the linkages between pairs of amino acid residues may independently be selected to be any one of a number of chemical linkages commonly used in peptide mimetic compounds. As such, suitable linkages in addition to the typical amide bond include vinyl, ether, ketomethylene, methylketo, methylamine, aminomethyl, methylene, ethylene, cyclopropylene, thioamide, and sulfonamide. Other linkages may also be suitable as long as the linkage allows for advantageous binding of Y to the substrate recognition site such that the sulfonyl imidazole group is oriented to react with the protease active site serine residue. As is known in the art, peptide analogs having one or more pairs of amino acids joined by these types of alternative linkages emulate the spatial structure of amide bonded peptide chains to a degree that still allows the analog to bind to other biomolecules with binding constants at least approaching those of the corresponding amide linked peptide). Such peptide analogs, with one or more non-peptide linkages, can be used to advantage in changing the reactivity of the bonds between amino acid residues as compared to amide bonds. These varying linkages can be selected and used by one of ordinary skill in the art to effect the in vivo and in vitro half lives of compounds as desired.

In another embodiment of the present invention, Y is of the Formula

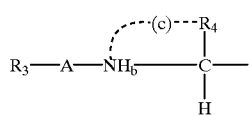

II wherein $R_3$ is hydrogen or an N-terminal blocking group, A is an amino acid chain of from 0–11 amino acid residues, $R_4$ is an amino acid side chain, b=0 or 1, and c is a covalent bond when b=0 and c is not a covalent bond when b=1.

When $R_3$ is an N-terminal blocking group, suitable blocking groups include those commonly known in the art, provided they do not adversely interfere with the specific activity of the inhibitor. N-terminal blocking groups may be beneficial in the synthesis of the compounds of the present invention and may be used to advantage in in vivo and in vitro uses where the reactivity of the N-terminal amino group may interfere through side reactions or would increase the compound's susceptibility to degradation.

Typical N-terminal end blocking groups that may be suitable for use in the present invention include but are not limited to formyl, acetyl, trifluoroacetyl, chloroacetyl, benzoyl, benzyloxycarbonyl, glutaryl, t-butoxycarbonyl, isopropyloxycarbonyl, succinyl, methoxysuccinyl, D-Proline, D-Valine, D-Alanine, D-Leucine, D-Phenylalanine, benzyl, and benzoylglycine. Particularly common N-terminal end blocking groups are formyl, acetyl, benzyloxycarbonyl, succinyl, methoxysuccinyl, and benzyl.

Additional suitable N-terminal blocking groups may include, but are not limited to methyl, ethyl, ethoxycarbonyl, fluorenylmethoxycarbonyl, allyloxycarbonyl, substituted benzyloxycarbonyl, acetoacetyl, phthaloxy, phenoxycarbonyl, p-methoxybenzenesulfonyl, p-toluenesulfonyl, isovaleroyl, methanesulfonyl, adipyl, suberyl, phthalamido, morpholinocarbonyl, azelayl, dansyl, tosyl, 2,4-dinitrophenyl, methoxyazelayl, methoxyadipyl, methoxysuberyl, 1-adamantanesulfonyl, 1-adamantaneacetyl, 2-carbobenzoyl, phenylacetyl, t-butylacetyl, thioproline, and bis[(1-methyl)methyl]acetyl.

$R_4$ may be either one of the naturally occurring amino acid side chains, or may alternatively be a side chain not normally occurring in nature. In a preferred embodiment, $R_4$ and each other amino acid side chain in the amino acid chain, if any, is independently selected from the group consisting of substituted or unsubstituted $C_1$–$C_{10}$ alkyl, $C_2$–$C_{10}$ alkenyl, $C_2$–$C_{10}$ alkynyl, $C_1$–$C_{10}$ alkoxy, aryl, aryloxy, $C_7$–$C_{12}$ alkaryl, $C_7$–$C_{12}$ aralkyl, $C_3$–$C_{10}$ cycloalkyl, $C_3$–$C_{10}$ cycloalkenyl, biphenyl, $C_2$–$C_{12}$ alkoxyalkyl, $C_1$–$C_6$ alkylsulfinyl, $C_1$–$C_{10}$ alkylsulfonyl, alkoxyaryl, aryloxyalkyl, nitro, nitroalkyl, heterocycle having 5–15 ring atoms in 1–3 rings and containing at least one heteroatom selected from the group consisting of oxygen, nitrogen and sulfur and having 0–7 double bonds and wherein one ring may include the alpha carbon and main chain nitrogen of the amino acid residue, wherein substituted means the addition of one or more groups selected from the group consisting of $C_1$–$C_{10}$ alkyl, hydroxy, amino, $C_1$–$C_{10}$ alkylamino, nitro, nitrile, guanidino, $C_1$–$C_{10}$ alkylnitro, sulfinyl, sulfonyl, alkylthio, thiol, and halo.

The number and sequence of amino acid residues in compounds of the present invention may be tailored to selectively bind to the substrate recognition site of a specific serine protease or subfamily of serine proteases desired to be inhibited. Amino acid sequences recognized by various serine proteases are well known in the art and are suitable for use in tailoring specific protease inhibitors of the present invention to specific proteases. New sequences specific for known and newly discovered serine proteases are continually being elucidated. Such information can be readily used to tailor serine protease inhibitor compounds specific for any given serine protease according to the present invention.

Exemplary of sulfonyl imidazolides of the present invention specific for given proteases would be imidazolesulfonylmethyl peptides with the amino acid sequences Ala-Ala-Ala; Ala-Ala-Pro-Val (SEQ ID NO:1); and Gly-Leu-Phe. Ala-Ala-Ala is known to bind generally to the elastase sub-family of serine proteases, which includes among others, leukocyte elastase, pancreatic elastase and neutrophile elastase, with variants in several mammalian species including human. As such, selection of this sequence of amino acid residues as Y in formula I(a) or I(b) above, would make an imidazolesulfonylmethyl peptide specific for elastases. Ala-Ala-Pro-Val (SEQ ID NO:1) on the other hand, is more specific for human leukocyte elastase and so would be a suitable sequence for a protease inhibitor more specific for human leukocyte elastase. Likewise, selecting the amino acid sequence of Gly-Leu-Phe, which is specific for human cathepsin G, would provide an inhibitor more specific for human cathepsin G.

Additional amino acid sequences particularly suitable for inhibitor compounds of the present invention tailored for specific serine proteases are listed in Table 2. This list is non-inclusive and is meant by way of example only and not by way of limitation of the scope of the invention. Other proteases with known sequence specificities are known in the art or can normally be obtained without undue experimentation by one of ordinary skill in the art. As such, α-amino or peptidyl sulfonyl imidazolides according to the present invention with sequences corresponding to these and any other serine protease binding specificity are considered to be within the scope of the present invention.

TABLE 2

Selective Amino Acid Sequences for Various Serine Proteases.

| Serine Proteases | Selective Sequences |
| --- | --- |
| Chymase | Phe-Leu-Phe |
| Chymotrypsin | Ala-Ala-Pro-Phe (SEQ ID NO:2) |
| Clotting Factor IX | Glu(benzyl ester)-Gly-Arg |
| Clotting Factor X | Leu-Gly-Arg |
| Clotting Factor XII | Gln-Gly-Arg |
| Elastase (generally) | Ala-Ala-Ala |
| Furin | Arg-Val-Arg-Arg (SEQ ID NO:3) |
| Glandular Kallikrein | Val-Leu-Arg |
| Granzyme B | Ile-Glu-Xaa-Asp* (SEQ ID NO:4) |
|  | Asp-Glu-Val-Asp (SEQ ID NO:4, wherein Xaa is Val) |
|  | Ala-Ala-Asp |
| Human Leukocyte Elastase | Ala-Ala-Pro-Val (SEQ ID NO:1) |
| Human Cathepsin G | Gly-Leu-Phe |
| Kex 2 Endoprotease | Tyr-Lys-Arg |
| Plasma Kallikrein | Pro-Phe-Arg |
| Plasmin | Val-Leu-Lys |
| Plasminogen Activator | Gly-Gly-Arg |
| Thrombin | Phe-Pro-Arg |
| Trypsin | Lys |
|  | Phe-Arg |
| Tryptase | Val-Pro-Arg |
| Urokinase | Gly-Gly-Arg |

(*Xaa is an amino acid residue, preferably a naturally occurring amino acid residue.)

It is also useful to create series of inhibitor compounds according to the present invention having varying lengths of amino acid chains and varying sequences of amino acid side chains for use in biochemical experimentation, as for example, but without limitation, to characterize binding specificities of serine proteases and to otherwise study protease substrate recognition, binding reaction mechanisms, and cellular and tissue physiological roles and processes. The creation of such series of sulfonyl imidazolides is within the scope of the present invention.

It is also contemplated that additions of polypeptide chains, lipids, and/or polysaccharides to the N-terminus of the present protease inhibitor compounds will be within the scope of the invention. In particular, polypeptide chains may be joined to the N-terminal through protein fusion techniques. These additional polypeptides, lipids, and/or polysaccharides may serve to enhance the pharmacological efficacy of the instant protease inhibitors. For example, a polypeptide may be attached that would target and anchor the compound in mucus membranes, or cause the protease inhibitor to accumulate and remain in particular cell types or tissues, such as the lungs. In producing such analogs, care should be taken to select extensions that will not provoke an adverse immulogical response in the organism to which the protease inhibitor is administered. The methods of determining whether a biological molecule will provoke adverse immulogical response are known to those of ordinary skill in the art.

To inhibit a serine protease with an inhibitor compound of the present invention, the inhibitor compound is brought into contact with the protease, as for example, by mixing solutions of each. As the inhibitor compound binds non-covalently to the protease substrate recognition site, the local reaction conditions tend to thermodynamically favor the sulfonylation reaction with the active site serine, which reaction therefore proceeds spontaneously. Inhibition will therefore occur under most solution conditions and particularly under the normal substrate binding conditions of the target protease. Typical binding conditions for many serine proteases in aqueous solution are a pH between about 7 and about 9 and physiological ionic strength of about 120–170 mM. Increased ionic strength will tend to strengthen binding of inhibitor compounds dependant on hydrophobic interactions for specific binding to the protease of interest, but weaken binding of inhibitor compounds dependant on ionic and hydrogen bonding interactions for specific binding to the protease. Decreased ionic strength will tend to have the reciprocal effect. Systems can be tailored to optimize binding of a given inhibitor compound specifically for the serine protease of interest without undue experimentation. Likewise, inhibitor compounds can be tailored to take advantage of particular binding conditions of a given system to optimize inhibition of a protease of interest.

Given the relationship between binding and inhibition, it is preferred to react at least a stoichiometric amount of the inhibitor compound with the protease. Ratios of inhibitor to protease of less than 1:1 will result in incomplete inhibition. Ratios greater than 1:1 will increase the kinetics of the reaction, resulting in faster inhibition. Some molar excess of inhibitor is also preferred when complete inhibition of protease is desired to counter any loss of inhibitor compound through any non-specific reactions or degradation of the compound.

PHARMACEUTICAL FORMULATIONS AND USE

Another aspect of the present invention provides pharmaceutical compositions useful in the treatment of human and animal disease states characterized by an over-activity of one or more serine proteases, comprising a pharmaceutically acceptable carrier containing a therapeutically effective amount of a sulfonyl imidazolide inhibitor compound as described above. By therapeutically effective amount, it is meant that amount of compound necessary to counteract the over-activity of the target serine protease(s) implicated in the disease state. This amount would generally be equal to the overexpressed concentration of the enzyme or under-expressed concentration of endogenous protease inhibitor, times a factor to account for the bioavailability of the inhibitor compound to the target tissue. Excessive proteolytic enzyme activity and the bioavailability of a compound are commonly determined parameters. Based on these determinations for a particular usage and inhibitor compound or mixture of compounds to be administered, the dosage of protease inhibitor(s) necessary to neutralize the excess proteolytic enzyme can be determined. Such determinations are routinely made by those of ordinary skill in the art in determining therapeutic dosages in treating various disorders, including immunological disorders, and are within the ambit of tasks routinely performed by them without undue experimentation.

In general, serine protease inhibitors of the present invention will be administered in therapeutically effective amounts via any of the usual and acceptable modes known in the art, either singly or in combination with other serine protease inhibitors of the present invention or with other therapeutic agents. A therapeutically effective amount may vary widely depending on the severity of the disease, the age and relative health of the subject, the potency of the compound used, and other factors. Therapeutically effective amounts may range from about 10 micrograms per kilogram patient bodyweight per day (μg/kg/day) to about 10 milligrams per kilogram of patient bodyweight per day (μg/kg/day), more typically from about 100 μg/kg/day to about 1 mg/kg/day. Thus a therapeutically effective amount for an 80 kg human may range from about 1 mg/day to about 1,000 mg/day, more typically from about 10 mg/day to about 100 mg/day.

In general, the serine protease inhibitors of the present invention will be administered as pharmaceutical compositions by one of the following routes: oral, systemic (e.g., transdermal, intranasal, intrapulmonary, or by suppository) or parenteral (e.g., subcutaneous, intramuscular, or intravenous). Compositions can take the form of tablets, pills, capsules, capulets, semi-solids, powders, sustained release formulations, enteric encapsulated tablets or capsules, solutions, suspensions, elixirs, aerosols, or any other appropriate composition. These compositions comprise, in general, one or more serine protease inhibitor compounds as described above in combination with at least one pharmaceutically acceptable excipient.

Acceptable excipients are non-toxic, aid administration, and do not adversely effect the therapeutic benefit of the serine protease inhibitor. Such excipients may be any solid, liquid, semi-solid, and in the case of an aerosol composition, gaseous excipient or propellant, that is generally available to one of skill in the art.

Solid pharmaceutical excipients include, but are not limited to, starch, cellulose, talc, glucose, lactose, sucrose, gelatin, malt, rice, flour, chalk, silica gel, magnesium sterate, sodium sterate, glycerol monosterate, sodium chloride, dried skim milk, and the like. Liquid and semi-solid excipients include, but are not limited to water, ethanol, glycerol, propylene glycol, and various oils, including those of petroleum, animal, vegetable, or synthetic origin (e.g., peanut oil, soybean oil, mineral oil, sesame oil, etc.). Preferred liquid carriers, particularly for injectable solutions, include water, saline, aqueous dextrose, and glycols.

Compressed gases may be used to disperse the serine protease inhibitors of the present invention in aerosol form. Inert gases suitable for this purpose are nitrogen, carbon dioxide, nitrous oxide, etc. Other suitable pharmaceutical carriers and their formulations are described in A. R. Alfonso's *Reminton's Pharmaceutical Sciences*, 1985, 17$^{th}$ edition, Easton, Pa., Mack Publishing Company, which is hereby expressly incorporated by reference.

The amount of a serine protease inhibitor of the present invention in the composition may vary widely depending on the type of formulation, size of the unit dosage, kind of excipients and other factors known to those of skill in the art of pharmaceutical sciences. In general, the final composition will comprise from about 0.1% to about 10% serine protease inhibitor compound by weight of the composition, preferably about 1% to about 10% inhibitor compound by weight of the composition with the remainder being the excipient or excipients.

It is expected that pharmaceutical preparations containing one or more serine protease inhibitors of the present invention would contain appropriate pharmaceutically acceptable carriers, diluents, fillers, binders, and other excipients depending on the dosage form contemplated. For oral administration, steps must be taken to prevent degradation of the peptidyl compounds in the digestive tract. Enteric coated dosage forms are contemplated as one form suitable for oral administration. Parenteral administration would require formulations containing water or saline solution or other pharmaceutically acceptable suspension agents. It is also contemplated that pharmaceutical compositions containing the present protease inhibitors can be administered locally, as by injection or topical application to the skin and mucous membranes, such as in the eye, for treatment of localized enzyme imbalances. The inhibitors of the present invention may also be administered as an aerosol, particularly when applied to the lungs as in the treatment of emphysema or asthma.

To treat a mammalian disease state characterized by an overactivity of one or more serine proteases, the enzyme activity level is determined on the patient according to known standardized assays. An appropriate formulation and dosage level may then be determined and made. The pharmaceutical composition is then administered to the patient to effect contact of the protease inhibitor compound with the target serine protease to inhibit the protease activity to the extent of the overactivity of the enzyme. Therapeutic regimes may include single or multiple doses of the pharmaceutical composition.

SYNTHESIS OF SULFONYL IMIDAZOLIDE DERIVATIVES

The α-amino and peptidyl sulfonyl imidazolide compounds of the present invention may be synthesized by converting the C-terminal carboxy group of the desired amino acid (meaning herein the α-carboxy group of the amino acid) or amino acid chain to an imidazolesulfonylmethyl group. Traditional methods of effecting such a derivitization are generally too harsh to preserve the α-amino or peptide moieties and are prone to unwanted side reactions. It has now been discovered that conversion of a carboxy group to an imidazolesulfonylmethyl group may be effected through a series of relatively gentle reactions starting from the desired amino acid or amino acid chain, generating a thioic acid S-ester intermediate, which is chlorinated in the presence of water to give the corresponding chlorosulfonylmethyl intermediate, which is then reacted with imidazole to provide the desired imidazolesulfonylmethyl compound.

It is to be understood that the synthetic process of the present invention will find general application for converting free carboxy substituents on organic molecules to the corresponding sulfonylmethyl derivatives, particularly imidazolesulfonylmethyl derivatives. Furthermore, the present inventive process provides a gentle and high yielding general method for producing sulfonyl derivatives from thioic acid S-esters through the corresponding sulfonyl chloride intermediate.

The process for converting a carboxyl substituent on an organic molecule to a substituted or unsubstituted imidazolesulfonylmethyl group comprises the steps of:

i) reacting the molecule with an alkylchloroformate to produce an alkylformate anhydride intermediate;

ii) reducing the alkylformate anhydride intermediate with a borohydride salt to produce a hydroxymethyl intermediate;

iii) reacting the hydroxymethyl intermediate with an alkyl or arylsulfonyl chloride to produce a sulfonate intermediate;

iv) reacting the sulfonate intermediate with a cesium alkyl or arylcarbothioic acid to produce a thioic acid S-ester intermediate;

v) reacting the thioic acid S-ester intermediate with $Cl_2$ and water to produce a sulfonyl chloride intermediate; and vi) reacting the sulfonyl chloride intermediate with a substituted or unsubstituted imidazole to produce the imidazolesulfonylmethyl derivative.

Preferred organic molecules for use as starting reagents are amino acids, peptides, proteins, or analogs thereof. More preferred starting organic molecules are amino acid chains of from 1–12 amino acid residues. It is particularly preferred that any free amine groups, as for example the N-terminal amine group, be protected with N-terminal blocking groups to prevent side reactions. Likewise, it is preferred that carboxy moieties in the amino acid chain that are not to be derivatized be protected by carboxy protecting groups.

Suitable peptide N-blocking groups are well known in the art. A listing of common peptide N-blocking groups and how to add and remove them is found in Theodora W. Greene, *Protective groups in Organic Synthesis*, Ch. 7 (1981), John Wiley & Sons, Inc., New York, N.Y., incorporated herein by reference. Preferred N-blocking groups include, but are not limited to, formyl, acetyl, trifluoroacetyl, chloroacetyl, benzoyl, benzyloxycarbonyl, glutaryl, t-butoxycarbonyl, isopropyloxycarbonyl, succinyl, methoxysuccinyl, D-Proline, D-Valine, D-Alanine, D-Leucine, D-Phenylalanine, benzyl, and benzoylglycine.

Suitable carboxy protecting groups are likewise well known in the art and a listing of common groups and how to add and remove them is found in Theodora W. Greene, *Protective groups in Organic Synthesis*, Ch. 5 (1981), John Wiley & Sons, Inc., New York, N.Y., incorporated herein by reference. Preferable carboxy blocking groups include, but are not limited to, substituted and unsubstituted $C_1$–$C_6$ alkyl esters, $C_1$–$C_6$ allyl esters, substituted and unsubstituted benzyl esters, $C_7$–$C_{12}$ alkylaryl esters, and silyl esters.

Blocking groups may either be removed at the end of the synthetic process or kept in place in the finished product as desired and as best suits the intended compound use.

α-Amino and peptidyl sulfonyl imidazolide compounds of the present invention may be synthesized according to Synthetic Scheme I, wherein $A_{C\text{-}term}$ is the C-terminal amino acid residue, $A_1$ is a bond or the desired N-terminal amino acid of the peptidyl sulfonyl imidazolide, $A_i$ is an amino acid residue, n is 0 or a positive integer, and $R_3$ is an N-terminal blocking group. The protected amino acid or amino acid chain is dissolved, suspended, dispersed or emulsified, etc., in an organic solvent system. Preferred organic solvent systems comprise volatile, non-nucleophilic solvents that solubilize all reactants and products. Examples include without limitation, tetrahydrofuran (THF), dimethylformamide (DMF), dichloromethane, ethyl acetate, chloroform, dioxane, and mixtures thereof. A particularly preferred solvent is THF. In a preferred embodiment, the organic solvent is chilled, though not frozen, and kept under an inert atmosphere, as for example ≦0° C. under a nitrogen, argon or helium atmosphere.

Synthetic Scheme I

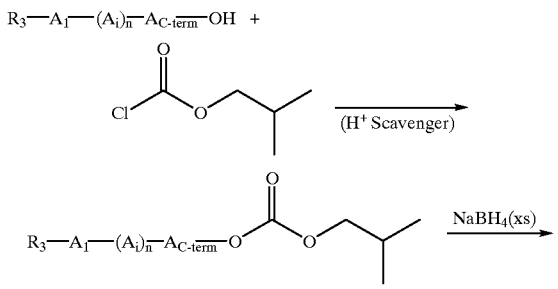

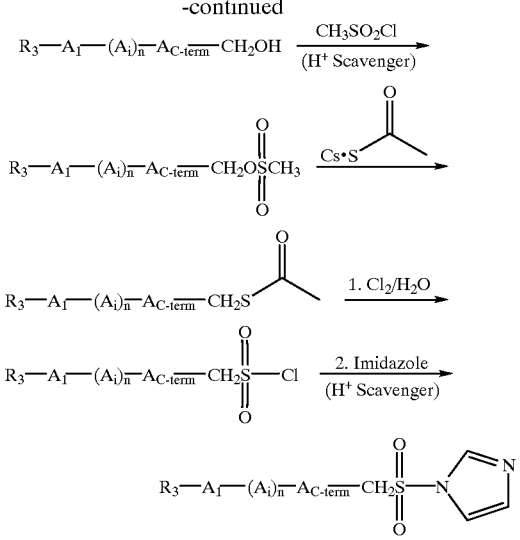

An alkylchloroformate is added to the solution and allowed to react with the amino acid or amino acid chain, preferably to completion to produce the corresponding alkylformate anhydride. Preferred alkyl moieties are branched and unbranched $C_1$–$C_6$ alkyl. A particularly preferred alkylchloroformate is isobutylchloroformate (IBCF).

In that the first step generates HCl, which inhibits the reaction, an amine base or equivalent acid scavenger is required in the reaction mixture to coordinate the liberated protons to obtain an acceptable yield of anhydride. Optimal results are achieved when the scavenger is present in at least about an equimolar ratio with the alkylchloroformate added. It is preferred that the alkylformate anhydride intermediate be worked up to remove the protonated base by standard procedures prior to the second step to avoid reacting with the added borohydride salt.

Preferred scavengers are tertiary amine bases that are soluble in the solvent system, as for example, but without limitation, NMM and TEA. NMM is particularly useful in that it is relatively mild and generally won't induce racemization of the amino acid or peptide chain. Furthermore, the protonated form of NMM precipitates for easy separation from the reaction mixture in preparation for the second step.

The alkylformate anhydride intermediate is next reduced to the corresponding α-amino or peptidyl hydroxymethyl intermediate with a borohydride salt under standard conditions, as for example, by the addition of a cold, aqueous solution of the borohydride salt. Many suitable borohydride salts are available commercially. A preferred borohydride salt is sodium borohydride ($NaBH_4$), because it is readily available, inexpensive, and relatively mild, in that it will generally reduce the anhydride, but not amides and other esters. The reduction reaction is allowed sufficient time to react, preferably to completion, to form the hydroxymethyl intermediate. Though isolation is not required, the hydroxymethyl intermediate may alternatively be isolated by art recognized means. By way of example, but without limitation, one typical work up includes treatment with a saturated sodium bicarbonate solution ($NaHCO_3$), extracting the solution with ethyl acetate (EtOAc), washing the organic portion first with 1M HCl, followed by saturated sodium bicarbonate and drying the organic fraction over anhydrous magnesium sulfate ($MgSO_4$). The product is then evaporated to dryness and purified over a silica gel column eluted with 95:5 EtOAc/MeOH. It is important for optimal yield to at least dry the hydroxymethyl intermediate in preparation for the next step to prevent water from decomposing the sulfonyl chloride reagent to be added.

The hydroxymethyl intermediate is then reacted with an alkyl- or aryl-sulfonyl chloride, preferably in an organic solvent, as for example, but without limitation, DMF, $CH_2CL_2$, ethylacetate, THF or mixtures thereof, to produce a sulfonate derivative of the amino acid or peptide. Preferred alkyl- and aryl-sulfonyl chlorides include without limitation, substituted and unsubstituted $C_1$–$C_{12}$ alkyl or aryl. Particularly preferred sulfonyl chlorides are methane-, ethane- and toluene-sulfonyl chloride. Methane- and ethane-sulfonyl chloride are especially preferred in that they are inexpensive and produce water soluble reaction by-products, which are easily removed during purification.

In that HCl is again produced as a by-product of the reaction, optimal yields are obtained when the reaction is run in the presence of an acid scavenger, such as a tertiary amine base, preferably in a molar ratio with the sulfonyl chloride of at least about 1.

The sulfonate intermediate may likewise alternatively be isolated and purified by art recognized means, though isolation is not required. It is, however preferable to remove the protonated acid scavenger and dry the intermediate before the next step.

The sulfonate intermediate is next reacted with cesium alkyl- or aryl-carbothioic acid, preferably in an organic solvent, to produce the corresponding thioic acid S-ester intermediate. Preferred cesium alkyl- or aryl-carbothioic acids include without limitation, $C_2$–$C_{12}$ alkyl, aryl, alkylaryl and arylalkyl, as for example, cesium thiolacetic acid and cesium thiobenzoic acid. Cesium thiolacetic acid is inexpensive and water soluble for easy purification from the reaction mixture. Again, the thioic acid S-ester intermediate may alternatively be isolated, though isolation is not completely necessary. It is preferred that excess cesium carbothioic acid be removed and to exchange solvents to a non-miscible solvent system.

Cesium thiolacetic acid may be produced by art recognized means, as for example, but without limitation, by adding cesium carbonate to a methanol solution of thiolacetic acid and stirring for a sufficient time to complete the reaction, as for example about five minutes at room temperature. The methanol is then evaporated and the resulting solid washed with acetone and dried by evaporation. The purified cesium thiolacetic acid is preferably immediately dissolved in an organic solvent, as for example DMF, DMSO or N,N-dimethylacetamide, and used in the reaction with the sulfonate intermediate.

In the novel final two steps of the synthetic method of the present invention, the thioic acid S-ester intermediate is converted to a highly reactive α-amino or peptidyl chlorosulfonylmethyl intermediate by chlorinating the thioic acid S-ester in the presence of added water. The chlorosulfonylmethyl intermediate is then reacted with substituted or unsubstituted imidazole to provide the final peptidyl imidazolesulfonylmethyl derivative.

In a preferred embodiment, the chlorination is conducted by bubbling chlorine gas through a liquid comprising the thioic acid S-ester and water. By way of example, but without limitation, the purified thioic acid S-ester intermediate may be dissolved in methlene chloride or chloroform followed by the addition of water, as for example, an equal volume of water as organic solvent. For optimal yields, preferred solvent system are not miscible with water so as to prevent the added water from precipitating either the thioic acid S-ester or the sulfonyl chloride intermediates, and from degrading the sulfonyl chloride intermediate. Vigorously stirring the biphasic system while bubbling chlorine gas through the system provides reactive access to the water and chlorine without precipitating intermediates and without over exposing the sulfonyl chloride product to the degradative effects of the water. The reaction is run for a time sufficient to essentially complete conversion of the thioic acid S-ester intermediate to the corresponding chlorosulfonylmethyl intermediate. Though not necessary, optimal yields are obtained by work up of the chlorosulfonylmethyl intermediate to remove water (degrades the sulfonyl chloride), excess $Cl_2$ (chlorinates the nucleophile to be added), and to concentrate the intermediate.

Lastly, the chlorosulfonylmethyl intermediate is reacted with substituted or unsubstituted imidazole to produce the desired imidazolesulfonylmethyl compound. Suitable substitutions on the imidazole carbons include branched or unbranched, $C_1$–$C_{12}$ alkyl, aryl, alkaryl, aralkyl or acyl. These substitutions may also include the incorporation of one or more groups selected from the group consisting of hydroxy, amino, nitro, nitrile, guanidino, sulfinyl, sulfonyl, thiol, and halo, provided that none of the substitutions interfere with the addition reaction or the intended function of the compound as an inhibitor. Optionally, one of the imidazole nitrogen atoms may also be substituted with a branched or unbranched $C_1$–$C_6$ alkyl group.

In a preferred embodiment, at least an equimolar amount of imidazole is added to the chlorosulfonylmethyl intermediate. By way of example, but without limitation, the imidazole may dissolved in methylene chloride, the solution added to the chlorosulfonylmethyl intermediate solution at 0° C. and allowed to react for about 30 minutes, as for example between about 15–45 minutes.

In that the nucleophilic replacement reaction liberates HCl, which will inhibit the reaction, optimal yields require the presence of an amine base or equivalent acid scavenger to coordinate the released protons, as for example, the addition of tertiary amines such as NMM and TEA. However, imidazole itself may also act as an efficient acid scavenger. As such, the addition of an equimolar excess of imidazole (i.e. addition of twice the amount of imidazole otherwise used) provides the most convenient form of scavenger, while simplifying purification of the end product.

Preferred reaction conditions include a molar ratio of added water to thioic acid S-ester of at least about 2, a molar ratio of $Cl_2$ to thioic acid S-ester of at least about 3, a molar ratio of imidazole to sulfonyl chloride of at least about 1, and a molar ratio of acid scavenger to imidazole of at least about 1 (i.e. when imidazole is used as the acid scavenger, the molar ratio of total imidazole to sulfonyl chloride of at least about 2).

The final α-amino or peptidyl sulfonyl imidazolide can be purified by art recognized means. By way of example, but without limitation, methylene chloride may be added to the final reaction mixture, which is then washed with HCl, washed with saturated sodium bicarbonate, washed with water, and then dried over anhydrous magnesium sulfate before evaporating the solvent to provide a dry white solid product.

In another embodiment of the present invention, the amino acid chain of the inhibitor compounds can be extended at any one of several steps throughout the synthetic method. In the embodiment described above, the amino acid chain is synthesized and reactive side chains blocked to provide a starting reagent for the first step of the synthesis. (See Synthetic Scheme I). In an alternative synthetic route, the synthesis can begin with the desired C-terminal amino acid with its alpha-amino group protected. The synthesis then proceeds through the synthetic scheme as described above, to the production of the corresponding thioic acid S-ester. At that point, the amino acid chain can be extended by art known means, as for example, but without limitation, by deprotecting the α-amino group of the thioic acid S-ester followed by reacting the thioic acid S-ester with a carboxy activated form of the remainder of the desired amino acid chain, as for example, but without limitation, a N-terminal protected peptidylic isobutyloxy formic anhydride in an organic solvent, preferably in the presence of an amine base, such as NMM, or equivalent acid scavenger. The resulting N-terminal protected peptidyl thioic acid S-ester is then reacted with chlorine gas in the presence of water, followed by addition of imidazole as described above in Synthetic Scheme I. (See Synthetic Scheme II, wherein $A_{C\text{-}term}$ is the C-terminal amino acid residue, $A_1$ is a bond or the desired N-terminal amino acid of the peptidyl sulfonyl imidazolide, $A_i$ is an amino acid residue, n is 0 or a positive integer, and $R_3$ and $R_3'$ are the same or different N-terminal blocking groups).

Synthetic Scheme II

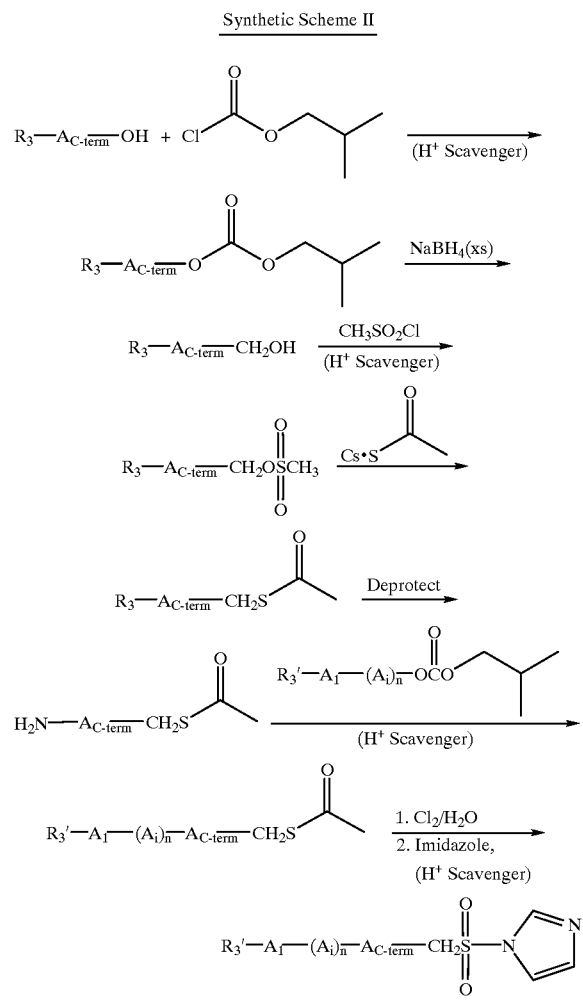

As a second alternative synthetic route, the N-protected C-terminal amino acid is reacted with an alkylchloroformate followed by reduction with a borohydride salt as described above in Synthetic Scheme I, to produce the desired N-protected α-amino-α-hydroxymethyl intermediate. The α-amino-α-hydroxymethyl intermediate may then be deprotected and subjected to a chain extension reaction as is commonly known in the art, to produce the full N-protected peptidyl hydroxymethyl intermediate, which is then processed as described above in Synthetic Scheme I to produce the desired sulfonyl imidazolide compound. (See Synthetic Scheme III, wherein $A_{C\text{-}term}$ is the C-terminal amino acid residue, $A_1$ is a bond or the desired N-terminal amino acid residue of the peptidyl sulfonyl imidazolide, $A_i$ is an amino acid residue, n is 0 or a positive integer, and R3 and R3' are N-terminal blocking groups).

Synthetic Scheme III

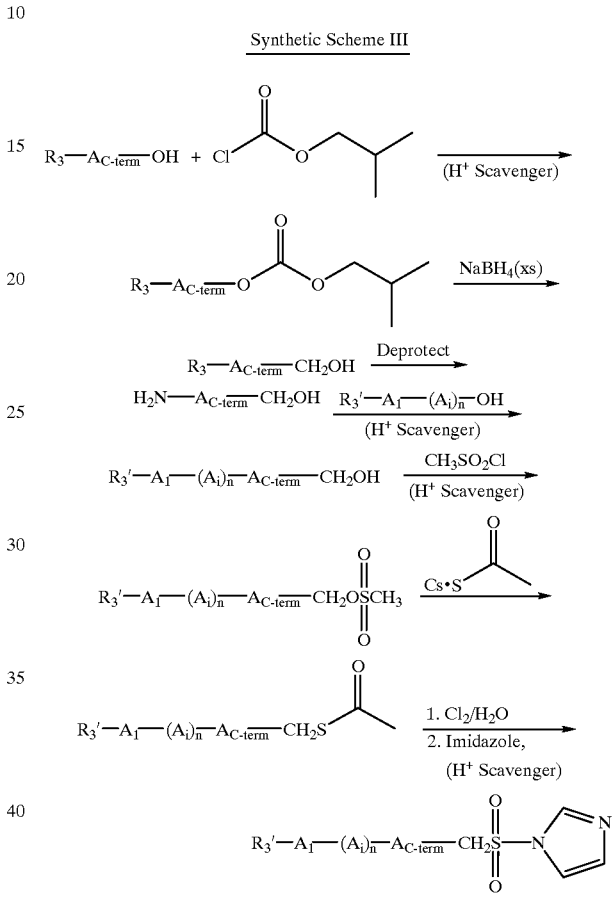

By way of example, but without limitation, the chain extension can be effected by deprotecting the peptidyl hydroxymethyl intermediate and then reacting it with an N-protected amino acid chain corresponding to the remainder of the desired amino acid chain sequence for the final inhibitor compound, in an organic solvent and in the presence of hydroxybenzoltriazole (HOBT), dicyclohexylcarbodiimide (DCC), and TEA. This reaction provides the N-protected peptidyl hydroxymethyl intermediate desired for continued processing as described above.

SYNTHESIS OF SULFONYL DERIVATIVES

It is to be understood that other α-amino or peptidyl sulfonyl derivatives may be made with the above-described synthetic process by introducing other desired nucleophiles in place of an imidazole compound in the last step of the synthesis after the production of the chlorosulfonylmethyl intermediate. Particularly suitable nucleophiles for use in the present synthetic method include, but are not limited to, imidazole, pyrazole, benzimidazole, benzotriazole, 1,2,3-triazole and 1,2,4-triazole. These and other suitable nucleophiles will have a range of reactivities as leaving groups from the sulfonyl derivative. It is therefore possible to tailor the reactivity of a compound as desired by election of a specific leaving group. The latter described extension of the synthetic method of the present invention may be of general use in the chemical arts for producing peptidyl sulfonyl derivatives that are not necessarily serine protease inhibitors.

The efficient and gentle method of producing sulfonyl derivatives from thioic acid S-esters through a chlorosulfonyl intermediate as described in the synthetic methods above is of general interest and utility in the chemical arts. Generally, any thioic acid S-ester can be reacted with $Cl_2$ and water to produce the corresponding chlorosulfonyl intermediate, preferably by bubbling chlorine gas through a liquid comprising the thioic acid S-ester and water. The highly reactive chlorosulfonyl intermediate is then converted to the desired sulfonyl derivative by reacting it with the appropriate nucleophile. In a preferred embodiment, the molar ratio of water used to treat the thioic acid S-ester solution to the thioic acid S-ester in solution is at least about 2, the molar ratio of chlorine gas to thioic acid S-ester is at least about 3, and the molar ratio of nucleophile to chlorosulfonyl is at least about 1. Generally, optimal reaction yields for the nucleophile addition will require the presence of an amine base or equivalent acid scavenger, preferably in at least an equimolar amount with the nucleophile, to coordinate the generated protons. As with imidazole in the production of sulfonyl imidazolides above, the nucleophile will often be an efficient acid scavenger. In such cases, the preferred reaction will generally be to simply add at least two molar equivalents of the nucleophile to the sulfonyl chloride, one equivalent for the addition, with the second functioning as the acid scavenger.

Preferred nucleophiles include, but are not limited to imidazole, pyrazole, benzimidazole, benzotriazole, 1,2,3-triazole and 1,2,4-triazole.

In a preferred embodiment of the synthetic method, the thioic acid S-ester is first dissolved in an organic solvent. The resulting solution is then treated with water, as for example, by adding the desired amount of water, preferably at least 2 molar equivalents of water to thioic acid S-ester in solution, followed by vigorous stirring. Chlorine gas is then bubbled through the solution with continued agitation to produce the corresponding chlorosulfonyl intermediate. As in the production of sulfonyl imidazolides above, it is preferred to select a biphasic solvent system of water and a water immiscible organic solvent to run the chlorination reaction in to minimize the exposure of the generated sulfonyl chloride to excess water. Vigorously stirring the biphasic system while bubbling chlorine gas through the system provides reactive access to the water and chlorine without precipitating intermediates and without over exposing the sulfonyl chloride product to the degradative effects of the water. In a preferred embodiment, the sulfonyl chloride intermediate is worked up by removing excess water to prevent degradation of the sulfonyl chloride. The nucleophile is then added to the solution to produce the desired sulfonyl derivative.

While the preferred embodiments of the invention have been described in detail in the foregoing description, the same is to be considered as illustrative and not restrictive in character, it being understood that only the preferred embodiments have been shown and described. The invention will now be further described with reference to the following specific Examples. It will be understood that these Examples are also only illustrative and are intended only to provide further understanding of the compositions and processes of the present invention.

EXAMPLE 1

Z-Ala-Ala-AlaCH$_2$SO$_2$-Im (a general inhibitor of the elastase subfamily of serine proteases) was synthesized according to the following steps:

Z-Ala-Ala-AlaCH$_2$OH: To 5 g (0.014 mol) of Z-Ala-Ala-AlaOH dissolved in THF/DMF 1:1 (50 mL) at −10° C. under a N$_2$ atmosphere were added 1.6 mL (0.014 mol) NMM and 1.9 mL (0.014 mol) IBCF. The reaction mixture was stirred 15 minutes, filtered, and the filtrate added slowly to an ice-cold solution of NaBH$_4$ (1.4 g, 0.037 mol) in H$_2$O (3 mL) and stirred 1 hour at ice-bath temperature and 1 hour at room temperature. The reaction mixture was cooled to 0° C. and treated with saturated NaHCO$_3$ solution, extracted with EtOAc, washed with 1M HCl that is saturated with NaHCO$_3$, dried over anhydrous MgSO$_4$, and evaporated to dryness. The crude product was purified over a silica gel column eluted with 95:5 EtOAc/MeOH to give 1.2 g product.

Z-Ala-Ala-AlaCH$_2$OSO$_2$Me: To a solution of Z-Ala-Ala-AlaCH$_2$OH (1.02 g, 2.9 mmol) in DMF (15 mL) at 0° C. were added TEA (0.33 mL, 2.9 mmol) and methanesulfonyl chloride (0.225 mL, 2.9 mmol) in 5 mL DMF. The reaction mixture was stirred at 0° C. for 5 minutes. The reaction mixture was diluted with EtOAc (100 mL), washed with 1M HCl, washed with water, dried over anhydrous MgSO$_4$ and evaporated to give 0.92 g of the mesylate.

CsSCOMe: Cesium carbonate (2.5 g, 7.7 mmol) was added to a methanol solution (20 mL) of thiolacetic acid (1.2 mL, 15.8 mmol) and stirred 5 minutes to provide a homogeneous solution. The methanol was evaporated, the yellow solid washed 5 times with acetone, decanted, and evaporated to dryness to yield a white solid. The solid was taken up immediately in DMF (10 mL) to be used in the next reaction.

Z-Ala-Ala-AlaCH$_2$SCOMe: To Z-Ala-Ala-AlaCH$_2$OSO$_2$Me (0.9 g, 2 mmol) was added a DMF (10 mL) solution of CsSCOMe (1–4 g, 6.8 mmol). The reaction mixture was stirred for 12 hours at room temperature. A white salt precipitated. The reaction mixture was treated with 1:1 H$_2$O/EtOAc (50 mL), the organic layer separated, washed with 1M HCl saturated with NaHCO$_3$, dried over anhydrous MgSO$_4$, evaporated, and pumped to dryness. The product was purified over a silica gel column eluted with EtOAc to give 0.28 g.

Z-Ala-Ala-AlaCH$_2$SO$_2$-Im: Z-Ala-Ala-AlaCH$_2$SCOMe (0.28 g, 0.7 mmol) was dissolved in CH$_2$Cl$_2$ (10 mL) and treated with H$_2$O (10 mL). The solution was stirred vigorously at 0° C. while Cl$_2$ gas was bubbled in for 30 minutes. The solution was then stirred for 30 minutes without further addition of Cl$_2$ gas. CH$_2$Cl$_2$ (10 mL) was added and the organic layer separated, washed with water, and dried over anhydrous MgSO$_4$. The dry solution was concentrated to about 5 mL by evaporation, cooled to 0° C., treated with imidazole (95 mg, 1.4 mmol), and stirred 2 hours with gradual warming to room temperature. CH$_2$Cl$_2$ (10 mL) was added to the reaction mixture, which was then washed with 1M HCl saturated with NaHCO$_3$, washed with water, dried over anhydrous MgSO$_4$, and evaporated to dryness to give a white solid (82 mg). The solid was assayed by NMR and mass spectroscopy and found to be Z-Ala-Ala-AlaCH$_2$SO$_2$-Im.

EXAMPLE 2

Inhibition of Human Leukocyte elastase by Z-Ala-Ala-AlaCH$_2$SO$_2$-imidazole.

Z-Ala-Ala-AlaCH$_2$SO$_2$-Im, prepared as in Example 1, was assayed for serine protease inhibition activity against human leukocyte elastase. Various concentrations of inhibitor were rapidly mixed with fixed aliquots of enzyme and allowed to react for at least two half-lives. Aliquots of the treated enzyme were then assayed spectrophotometrically for protease activity using MeOSuc-Ala-Ala-Pro-Val-AMC as the substrate to determine $k_{obs}/[I]$. With an enzyme concentration 200 µM, substrate concentration of 100 µM and inhibitor concentration of 200 µM, the measure $k_{obs}$ was 0.0025 s$^{-1}$ ($k_{obs}/[I]$=12.7 M$^{-1}$s$^{-1}$). This was 45 times more potent than the corresponding peptidyl chloromethane inhibitor as reported in Tuhy, P. M. and Powers, J. C., FEBS Letters, Vol. 50, No. 3, pg. 359–361 (1975), incorporated herein by reference.

EXAMPLE 3

MeOSuc-Ala-Ala-Pro-ValCH$_2$SO$_2$-Imidizole (a specific inhibitor of human leukocyte elastase) is synthesized according to the following steps:

Boc-ValCH$_2$OH: To 5 g (0.023 mol) of Boc-Valine dissolved in THF (30 mL) at −10° C. under N$_2$ are added NMM (2.5 mL 0.023 mol) and IBCF (3 mL, 0.023 mol). The reaction mixture is stirred 15 minutes and filtered. The filtrate is added slowly to an ice-cold solution of NaBH$_4$ (2.3 g, 0.061 mol) in H$_2$O (10 mL) and stirred 1 hour at ice-bath temperature then 1 hour at room temperature. The reaction mixture is cooled to 0° C. and treated with saturated NaHCO$_3$ solution, extracted with EtOAc, washed with 1M HCl saturated with NaHCO$_3$, dried over anhydrous MgSO$_4$, and evaporated to dryness. The crude Boc-ValCH$_2$OH product is purified over a silica gel column eluted with 95:5 EtOAc/MeOH.

Boc-ValCH$_2$OSO$_2$Me: To a solution of Boc-ValCH$_2$OH (1 g, 4.3 mmol) in CH$_2$Cl$_2$ (20 mL) at 0° C. are added TEA (0.5 mL, 4.3 mmol) and methanesulfonyl chloride (0.34 mL, 4.3 mmol) in 5 mL CH$_2$Cl$_2$. The reaction mixture is stirred at 0° C. for 5 min. and then diluted with CH$_2$Cl$_2$ (50 mL), washed with 1M HCl, washed with water, dried over anhydrous MgSO$_4$, and evaporated to dryness to give the mesylate.

CsSCOMe: Cesium carbonate (2.5 g, 7.7 mmol) is added to a methanol solution (20 mL) of thiolacetic acid (1.2 mL, 15.8 mmol) and stirred 5 minutes to provide a homogeneous solution. The methanol is evaporated, the yellow solid washed 5 times with acetone, decanted, and evaporated to dryness to yield a white solid after pumping to dryness. The solid is taken up immediately in DMF (10 mL) to be used in the next reaction.

Boc-ValCH$_2$SCOMe: To Boc-ValCH$_2$OSO$_2$Me (0.62 g, 2 mmol) is added a DMF (10 mL) solution of CsSCOMe (1.4 g, 6.8 mmol) and the reaction mixture stirred 12 hour at room temperature. A white salt precipitates. The mixture is treated with a 1:1 of H$_2$O/EtOAc (50 mL), the organic layer separated, washed with 1M HCl saturated with NaHCO$_3$, dried over anhydrous MgSO$_4$, and evaporated to dryness. The product is purified over a silica gel column eluted with EtOAc to give the thiol ester.

HCl·HValCH$_2$SCOMe: Boc-ValCH$_2$SCOMe (0.5 g, 1.7 mmol) is treated with 1M HCl in dioxane (5 mL) for 30 minutes at 0° C. and then diluted with ether (50 mL). The white solid is filtered and pumped dry.

MeOSuc-Ala-Ala-Pro-ValCH$_2$SCOMe: To MeOSuc-Ala-Ala-ProOH (0.64 g, 1.7 mmol) in THF (5 mL) at −10° C. are added NMM (0.19 mL, 1.7 mmol) and IBCF (0.22 mL, 1.7 mmol). The reaction mixture is stirred for 5 minutes. A DMF (5 mL) solution of HCl·HValCH$_2$SCOMe (0.34 g, 1.7 mmol) and NMM (19 mL, 1.7 mmol) are added and stirred 1 hour with gradual warming to room temperature. The reaction mixture is diluted with EtOAc (30 mL), washed with 1M HCl saturated with NaHCO$_3$, washed with water, dried over anhydrous MgSO$_4$ and evaporated to dryness. The product is purified over a silica gel column eluted with EtOAc.

MeOSuc-Ala-Ala-Pro-ValCH$_2$SO$_2$-Im: MeOSuc-Ala-Ala-Pro-ValCH$_2$SCOMe (0.51 g, 1 mmol) is dissolved in CH$_2$Cl$_2$ (20 mL) and treated with H$_2$O (10 mL). The solution is stirred vigorously at 0° C. while Cl$_2$ gas is bubbled in for 30 minutes. The reaction mixture is then stirred for 30 minutes without further addition of Cl$_2$ gas. CH$_2$Cl$_2$ (10 mL) is added and the organic layer separated, washed with water, and dried over anhydrous MgSO$_4$. The dry solution is concentrated to about 10 mL by evaporation, cooled to 0° C. treated with imidazole (135 mg, 2 mmol), and stirred 2 hour with gradual warming to room temperature. CH$_2$Cl$_2$ (10 mL) is added to the reaction mixture, which is then washed with 1M HCl saturated with NaHCO$_3$, washed with water, dried over anhydrous MgSO$_4$, and evaporated to give MeOSuc-Ala-Ala-Pro-ValCH$_2$SO$_2$-Im.

EXAMPLE 4

Inhibition of human leukocyte elastase by MeOSuc-Ala-Ala-Pro-ValCH$_2$SO$_2$-imidazole.

MeOSuc-Ala-Ala-Pro-ValCH$_2$SO$_2$-Im is prepared as in example 3 and assayed as in Example 2 for inhibition of human leukocyte elastase and human cathepsin G with the corresponding peptidyl chloromethane, MeOSuc-Gly-Leu-PheCH$_2$SO$_2$-Im, and Z-Ala-Ala-AlaCH$_2$SO$_2$-Im as comparator inhibitors. The $k_{obs}/[I]$ for MeOSuc-Ala-Ala-Pro-ValCH$_2$SO$_2$-Im against human leukocyte elastase is significantly higher (more potent inhibitor) than for the comparator inhibitors. The $k_{obs}/[I]$ for MeOSuc-Ala-Ala-Pro-ValCH$_2$SO$_2$-Im against human cathepsin G is significantly lower (less potent inhibitor) than MeOSuc-Gly-Leu-PheCH$_2$SO$_2$-Im.

EXAMPLE 5

Z-Gly-Leu-PheCH$_2$SO$_2$-Im (a specific inhibitor of human cathepsin G) is synthesized according to the following steps:

Boc-PheCH$_2$OH: To 5.7 g (0.023 mol) of Boc-PheOH dissolved in THF (30 mL) at −10° C. under N$_2$ are added NMM (2.5 mL, 0.023 mol) and IBCF (3 mL, 0.023 mol). The reaction mixture is stirred for 15 minutes and filtered. The filtrate is slowly added to an ice-cold solution of NaBH$_4$ (2.3 g, 0.061 mol) in H$_2$O (10 mL) and then stirred for 1 hour at ice-bath temperature followed by stirring for 1 hour at room temperature. The reaction is cooled to 0° C., treated with saturated NaHCO$_3$ solution, extracted with EtOAc, washed with 1M HCl, washed with water, dried over anhydrous MgSO$_4$, and evaporated to dryness. The crude product is purified over a silica gel column eluted with 95:5 EtOAc/MeOH.

HCl·HPheCH$_2$OH: Boc-PheCH$_2$OH (0.5 g, 2 mmol) is treated with 1M HCl in dioxane (5 mL) for 30 minutes at 0° C. and then diluted with ether (50 mL). The white solid is filtered and pumped dry.

Z-Gly-Leu-PheCH$_2$OH: To Z-Gly-LeuOH (0.64 g, 2 mmol) in DMF (10 mL) are added HCl·HPheCH$_2$OH (0.38 g, 2 mmol), TEA (0.28 mL, 2 mmol) and hydroxybenzotriazole (0. 27, 2 mmol). The reaction mixture is cooled to 0° C. and dicyclohexylcarbodiimide (0.41 g, 2 mmol) is added. The reaction mixture is stirred 1 hour at 0° C. followed by stirring for 12 hours at room temperature. EtOAc (30 mL) is added and the mixture is filtered. The filtrate is washed with 1M HCl saturated with NaHCO$_3$, washed with water, dried over anhydrous MgSO$_4$, and evaporated to dryness. The product is purified over a silica gel column eluted with (95:5) EtOAc/MeOH.

Z-Gly-Leu-PheCH$_2$OSO$_2$Me: To a solution of Z-Gly-Leu-PheCH$_2$OH (0.5 g, 1 mmol) in CH$_2$Cl$_2$ (5 mL) at 0° C. are added TEA (0.12 mL, 1 mmol) and methanesulfonyl chloride (0.08 mL, 1 mmol) in CH$_2$Cl$_2$ (1 mL). The reaction mixture is stirred at 0° C. for 5 minutes and then diluted with CH$_2$Cl$_2$ (10 mL), washed with 1M HCl, washed with water, dried over anhydrous MgSO$_4$ and evaporated to dryness to give the mesylate.

CsSCOMe: Cesium carbonate (1.3 g, 3.9 mmol) is added to a methanol solution (10 mL) of thiolacetic acid (0.6 mL, 7.9 mmol) and stirred for 5 minutes to provide a homogeneous solution. The methanol is evaporated, the yellow solid washed 5 times with acetone, decanted, and evaporated to dryness to yield a white solid. The solid is taken up immediately in DMF (5 mL) to be used in the next reaction.

Z-Gly-Leu-PheCH$_2$SCOMe: To Z-Gly-Leu-PheCH$_2$OSO$_2$Me (0.53 g, 1 mmol) is added a DMF (5 mL) solution of CsSCOMe (0.7 g, 3.4 mmol) and the reaction mixture is stirred for 12 hours at room temperature. A white salt precipitates. The mixture is treated with a 1:1 mixture of H$_2$O and EtOAc (30 mL), the organic layer separated, washed with 1M HCl saturated with NaHCO$_3$, dried over anhydrous MgSO$_4$, and evaporated and pumped to dryness. The product is purified over a silica gel column eluted with EtOAc to give the thiol ester.

Z-Gly-Leu-PheCH$_2$SO$_2$-Im: Z-Gly-Leu-PheCH$_2$SCOMe (0.5 g, 1 mmol) is dissolved in CH$_2$Cl$_2$ (20 mL) and treated with H$_2$O (10 mL). The solution is stirred vigorously at 0° C. while Cl$_2$ gas is bubbled in for 30 minutes. The reaction mixture is then stirred 30 minutes without further addition of Cl$_2$ gas. CH$_2$Cl$_2$ (10 mL) is added and the organic layer separated, washed with water, and dried over anhydrous MgSO$_4$. The dry solution is concentrated to about 10 mL by evaporation, cooled to 0° C., treated with imidazole (135 mg, 2 mmol), and stirred for 2 hours with gradual warming to room temperature. CH$_2$Cl$_2$ (10 mL) is added to the reaction mixture, which is then washed with 1M HCl saturated with NaHCO$_3$, washed with water, dried over anhydrous MgSO$_4$, and evaporated to give Z-Gly-Leu-PheCH$_2$SO$_2$-Im.

EXAMPLE 6

Inhibition of human cathepsin G by Z-Gly-Leu-PheCH$_2$SO$_2$-Im.

Z-Gly-Leu-PheCH$_2$SO$_2$-Im is prepared as in Example 5, and is assayed as in Example 2 for inhibition of human cathepsin G and human leukocyte elastase with the corresponding peptidyl chloromethane, MeOSuc-Ala-Ala-Pro-ValCH$_2$SO$_2$-Im, and Z-Ala-Ala-AlaCH$_2$SO$_2$-Im as comparator inhibitors. The k$_{obs}$/[I] for Z-Gly-Leu-PheCH$_2$SO$_2$-Im against human cathepsin G is significantly higher (more potent inhibitor) than for the comparator inhibitors. The k$_{obs}$/[I] for Z-Gly-Leu-PheCH$_2$SO$_2$-Im against human leukocyte elastase is significantly lower (less potent inhibitor) than MeOSuc-Ala-Ala-Pro-ValCH$_2$SO$_2$-Im.

EXAMPLE 7

Z-Ala-Ala-AlaCH$_2$SO$_2$-1,2,4-triazole is synthesized as follows:

Z-Ala-Ala-AlaCH$_2$SCOMe is made as described in Example 1 above. The Z-Ala-Ala-AlaCH$_2$SCOMe (0.28 g, 0.7 mmol) is then dissolved in CH$_2$Cl$_2$ (10 mL) and treated with H$_2$O (10 mL). The solution is stirred vigorously at 0° C. while Cl$_2$ gas was bubbled in for 30 minutes. The solution is then stirred for 30 minutes without further addition of Cl$_2$ gas. CH$_2$Cl$_2$ (10 mL) is added and the organic layer separated, washed with water, and dried over anhydrous MgSO$_4$. The dry solution is concentrated to about 5 mL by evaporation, cooled to 0° C., treated with 1,2,4-triazole (96.7 mg, 1.4 mmol), and stirred 2 hours with gradual warming to room temperature. CH$_2$Cl$_2$ (10 mL) is added to the reaction mixture, which is then washed with 1M HCl saturated with NaHCO$_3$, washed with water, dried over anhydrous MgSO$_4$, and evaporated to dryness to give a white solid. The solid s assayed by NMR, mass spectroscopy, and IR and found to be Z-Ala-Ala-AlaCH$_2$SO$_2$-1,2,4-triazole.

EXAMPLE 8

Benzyloxycarbonyl-4-aminobenzyl-sulfonyl-benzotriazole.

Z—NH—C$_6$H$_4$—CH$_2$OH: To 3.60 g (0.014 mol) of 4-benzyloxycarbonyl-aminobenzoic acid dissolved in THF (50 mL) at −10° C. under a N$_2$ atmosphere are added 1.6 mL (0.014 mol) NMM and 1.9 mL (0.014 mol) IBCF. The reaction mixture is stirred 15 minutes, filtered, and the filtrate added slowly to an ice-cold solution of NaBH$_4$ (1.4 g, 0.037 mol) in H$_2$O (3 mL) and stirred 1 hour at ice-bath temperature and 1 hour at room temperature. The reaction mixture is cooled to 0° C. and treated with saturated NaHCO$_3$ solution, extracted with EtOAc, washed with 1M HCl that is saturated with NaHCO$_3$, dried over anhydrous MgSO$_4$, and evaporated to dryness.

Z—NH—C$_6$H$_4$—COSO$_2$Me: To a solution of Z—NH—C$_6$H$_4$—CH$_2$OH (2.9 mmol) in DMF (15 mL) at 0° C. are added TEA (0.33 mL, 2.9 mmol) and methanesulfonyl chloride (0.225 mL, 2.9 mmol) in 5 mL DMF. The reaction mixture is stirred at 0° C. for 5 minutes. The reaction mixture is diluted with EtOAc (100 mL), washed with 1M HCl, washed with water, dried over anhydrous MgSO$_4$ and evaporated to give Z—NH—C$_6$H$_4$—COSO$_2$Me.

Z—NH—C$_6$H$_4$—CH$_2$SCOMe: To Z—NH—C$_6$H$_4$—COSO$_2$Me (0.9 g, 2 mmol) is added a DMF (10 mL) solution of CsSCOMe (1–4 g, 6.8 mmol). The reaction mixture is stirred for 12 hours at room temperature. A white salt is precipitated. The reaction mixture is treated with 1:1 H$_2$O/EtOAc (50 mL), the organic layer separated, washed with 1M HCl saturated with NaHCO$_3$, dried over anhydrous MgSO$_4$, evaporated, and pumped to dryness. The product is purified over a silica gel column and is eluted with EtOAc to give Z—NH—C$_6$H$_4$—CH$_2$SCOMe.

Z—NH—C$_6$H$_4$—CH$_2$SO$_2$-benzotriazole: Z—NH—C$_6$H$_4$—CH$_2$SCOMe (0.7 mmol) is dissolved in CH$_2$Cl$_2$ (10 mL) and treated with H$_2$O (10 mL). The solution is stirred vigorously at 0° C. while Cl$_2$ gas is bubbled in for 30 minutes. The solution is then stirred for 30 minutes without further addition of Cl$_2$ gas. CH$_2$Cl$_2$ (10 mL) is added and the organic layer separated, washed with water, and dried over anhydrous MgSO$_4$. The dry solution is concentrated to about 5 mL by evaporation, cooled to 0° C., treated with benzotriazole (1.4 mmol), and stirred 2 hours with gradual warming to room temperature. CH$_2$Cl$_2$ (10 mL) is added to the reaction mixture, which is then washed with 1M HCl saturated with NaHCO$_3$, washed with water, dried over anhydrous MgSO$_4$, and evaporated to dryness to give a solid. The solid is assayed by NMR, mass spectroscopy, and IR and found to be benzyloxycarbonyl-4-aminobenzyl-sulfonyl-benzotriazole.

While the invention has been illustrated and described in detail in the foregoing description and figures, the same is to be considered as illustrative and not restrictive in character, it being understood that only the preferred embodiments have been shown and described and that all changes, equivalents, and modifications that come within the spirit of the invention as defined by the following claims are desired to be protected.

I claim:

1. An α-amino acid or peptidyl compound having a C-terminal imidazolesulfonylmethylene group, which is a serine protease inhibitor compound of the formula:

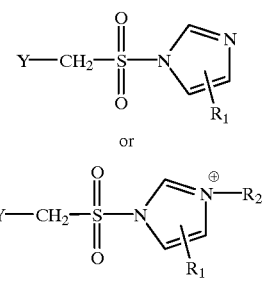

wherein Y is a group capable of interacting with the substrate recognition site of a serine protease, $R_1$ is hydrogen or branched or unbranched, substituted or unsubstituted $C_1$–$C_{12}$ alkyl, aryl, alkaryl, aralkyl or acyl substituent, wherein said substituted substituent is substituted with one or more functional moieties selected from the group consisting of: hydroxy, amino, nitro, nitrile, guanidino, sulfinyl, sulfonyl, thiol, and halo, and $R_2$ is branched or unbranched $C_1$–$C_6$ alkyl.

2. The compound of claim 1 wherein Y comprises an α-amino group, or an amino acid chain of from 2 to 12 amino acid residues.

3. The compound of claim 2 wherein Y is of the formula

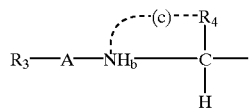

wherein $R_3$ is hydrogen or an N-terminal blocking group, A is an amino acid chain of from 0–11 amino acid residues, $R_4$ is an amino acid side chain, b=0 or 1, and c is a covalent bond when b=0 and c is not a covalent bond when b=1.

4. The compound of claim 3 wherein $R_4$ and each other amino acid side chain in the amino acid chain is independently selected from the group consisting of substituted or unsubstituted $C_1$–$C_{10}$ alkyl, $C_2$–$C_{10}$ alkenyl, $C_2$–$C_{10}$ alkynyl, $C_1$–$C_{10}$ alkoxy, aryl, aryloxy, $C_7$–$C_{12}$ alkaryl, $C_7$–$C_{12}$ aralkyl, $C_3$–$C_{10}$ cycloalkyl, $C_3$–$C_{10}$ cycloalkenyl, biphenyl, $C_2$–$C_{12}$ alkoxyalkyl, $C_1$–$C_6$ alkylsulfinyl, $C_1$–$C_{10}$ alkylsulfonyl, alkoxyaryl, aryloxyalkyl, nitro, nitroalkyl, heterocycle having 5–15 ring atoms in 1–3 rings and containing at least one heteroatom selected from the group consisting of oxygen, nitrogen and sulfur and having 0–7 double bonds and wherein one ring may include the alpha carbon and main chain nitrogen of the amino acid residue, wherein substituted means the addition of one or more groups selected from the group consisting of $C_1$–$C_{10}$ alkyl, hydroxy, amino, $C_1$–$C_{10}$ alkylamino, nitro, nitrile, guanidino, $C_1$–$C_{10}$ alkylnitro, sulfinyl, sulfonyl, alkylthio, thiol, and halo.

5. The compound of claim 3 wherein $R_3$ is an N-terminal blocking group selected from the group consisting of formyl, acetyl, trifluoroacetyl, chloroacetyl, benzoyl, benzyloxycarbonyl, glutaryl, t-butoxycarbonyl, isopropyloxycarbonyl, succinyl, methoxysuccinyl, D-Proline, D-Valine, D-Alanine, D-Leucine, D-Phenylalanine, benzyl, and benzoylglycine.

6. The compound of claim 5 wherein the N-terminal blocking group is selected from the group consisting of formyl, acetyl, benzyloxycarbonyl, succinyl, methoxysuccinyl, and benzyl.

7. The compound of claim 2 wherein the linkage between each pair of amino acid residues in the amino acid chain is bound together by a chemical linkage, each linkage being independently selected from the group of linkages consisting of amide, vinyl, ether, ketomethylene, methylketo, methylamine, aminomethyl, methylene, ethylene, cyclopropylene, thioamide and sulfonamide.

8. The compound of claim 2 wherein the α-amino group or the sequence of amino acid residues comprising Y is selected to selectively bind to the substrate recognition site of the protease to be inhibited.

9. The compound of claim 8 wherein Y comprises the amino acid residue sequence Ala-Ala-Ala.

10. The compound of claim 8 wherein Y comprises the amino acid residue sequence set forth in SEQ ID NO:1.

11. The compound of claim 8 wherein Y comprises the amino acid residue sequence Gly-Leu-Phe.

12. The compound of claim 8 wherein Y comprises the amino acid residue sequence Phe-Leu-Phe.

13. The compound of claim 8 wherein Y comprises the amino acid residue sequence set forth in SEQ ID NO:2.

14. The compound of claim 8 wherein Y comprises the amino acid residue sequence Glu(benzyl ester)-Gly-Arg.

15. The compound of claim 8 wherein Y comprises the amino acid residue sequence Leu-Gly-Arg.

16. The compound of claim 8 wherein Y comprises the amino acid residue sequence Gln-Gly-Arg.

17. The compound of claim 8 wherein Y comprises the amino acid residue sequence set forth in SEQ ID NO:3.

18. The compound of claim 8 wherein Y comprises the amino acid residue sequence Val-Leu-Arg.

19. The compound of claim 8 wherein Y comprises the amino acid residue sequence set forth in SEQ ID NO:4, wherein Xaa is an amino acid residue.

20. The compound of claims wherein Y comprises the amino acid residue sequence set forth in SEQ ID NO:4, wherein Xaa is Val.

21. The compound of claim 8 wherein Y comprises the amino acid residue sequence Ala-Ala-Asp.

22. The compound of claim 8 wherein Y comprises the amino acid residue sequence Tyr-Lys-Arg.

23. The compound of claim 8 wherein Y comprises the amino acid residue sequence Pro-Phe-Arg.

24. The compound of claim 8 wherein Y comprises the amino acid residue sequence Val-Leu-lys.

25. The compound of claim 8 wherein Y comprises the amino acid residue sequence Gly-Gly-Arg.

26. The compound of claim 8 wherein Y comprises the amino acid residue sequence Phe-Pro-Arg.

27. The compound of claim 8 wherein Y comprises the amino acid residue Lys.

28. The compound of claim 8 wherein Y comprises the amino acid residue sequence Phe-Arg.

29. The compound of claim 8 wherein Y comprises the amino acid residue sequence Val-Pro-Arg.

30. The compound of claim 8 wherein Y comprises the amino acid residue sequence Gly-Gly-Arg.

31. A pharmaceutical composition useful in the treatment of disease states characterized by an over-activity of one or more serine proteases comprising a pharmaceutically acceptable carrier containing a therapeutically effective amount of the serine protease inhibitor compound of claim 1.

32. The pharmaceutical composition of claim 31 wherein the serine protease inhibitor compound is of the formula

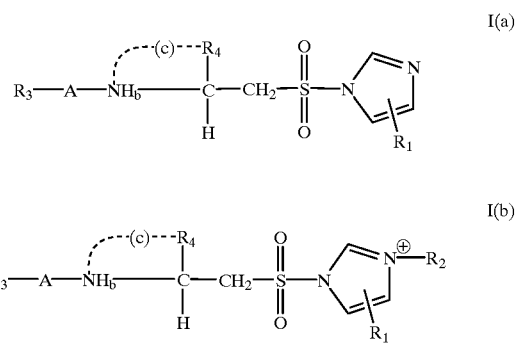

wherein $R_1$ is hydrogen or branched or unbranched, substituted or unsubstituted $C_1$–$C_{12}$ alkyl, aryl, alkaryl, aralkyl or acyl, $R_2$ is branched or unbranched $C_1$–$C_6$ alkyl, $R_3$ is hydrogen or an N-terminal blocking group, A is an amino acid chain of from 0–11 amino acid residues, $R_4$ is an amino acid side chain, b=0 or 1, and c is a covalent bond when b=0 and c is not a covalent bond when b=1.

33. The compound of claim 1 wherein Y comprises a naturally occurring amino acid or a non naturally occurring amino acid or both.

* * * * *

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Binding Site for Human  Leukocyte Elastase

<400> SEQUENCE: 1

Ala Ala Pro Val
1

<210> SEQ ID NO 2
<211> LENGTH: 4
<212> TYPE: PRT
<213> ORGANISM: Artificial Sequence
<220> FEATURE:
<223> OTHER INFORMATION: Binding Site for Chymo trypsin

<400> SEQUENCE: 2

Ala Ala Pro Phe
1

<210> SEQ ID NO 3
<211> LENGTH: 4
<212> TYPE: PRT
<213> ORGANISM: Artificial Sequence
<220> FEATURE:
<223> OTHER INFORMATION: Binding Site for Furin

<400> SEQUENCE: 3

Arg Val Arg Arg
1

<210> SEQ ID NO 4
<211> LENGTH: 4
<212> TYPE: PRT
<213> ORGANISM: Artificial Sequence
<220> FEATURE:
<221> NAME/KEY: VARIANT
<221> NAME/KEY: Position 3
<223> OTHER INFORMATION: Binding Site for Granz yme B; wherein Xaa is
      an amino acid residue

<400> SEQUENCE: 4

Arg Glu Xaa Asp
1